(12) United States Patent
Groff et al.

(10) Patent No.: US 11,540,838 B2
(45) Date of Patent: Jan. 3, 2023

(54) LEFT ATRIAL APPENDAGE IMPLANT WITH SEALING DISK

(71) Applicant: BOSTON SCIENTIFIC SCIMED, INC., Maple Grove, MN (US)

(72) Inventors: Joel N. Groff, Delano, MN (US); Patrick A. Haverkost, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 300 days.

(21) Appl. No.: 17/005,468

(22) Filed: Aug. 28, 2020

(65) Prior Publication Data
US 2021/0059685 A1 Mar. 4, 2021

Related U.S. Application Data

(60) Provisional application No. 62/894,296, filed on Aug. 30, 2019.

(51) Int. Cl.
*A61B 17/12* (2006.01)
(52) U.S. Cl.
CPC .. *A61B 17/12122* (2013.01); *A61B 17/12031* (2013.01); *A61B 17/12172* (2013.01)
(58) Field of Classification Search
CPC ........ A61B 17/12122; A61B 17/12031; A61B 17/12177; A61B 2017/12054; A61B 17/12
See application file for complete search history.

(56) References Cited

U.S. PATENT DOCUMENTS

| | | |
|---|---|---|
| 178,283 A | 6/1876 | French |
| 1,967,318 A | 7/1934 | Monahan |
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |

(Continued)

FOREIGN PATENT DOCUMENTS

| | | |
|---|---|---|
| CN | 1399571 A | 2/2003 |
| CN | 202143640 U | 2/2012 |

(Continued)

OTHER PUBLICATIONS

International Search Report and Written Opinion dated Aug. 3, 2004 for International Application No. PCT/US2004/008109.

(Continued)

*Primary Examiner* — George J Ulsh
(74) *Attorney, Agent, or Firm* — Seager, Tufte & Wickhem LLP

(57) ABSTRACT

An implant for occluding a left atrial appendage may include an expandable framework including a body portion and a disk portion, wherein the expandable framework is configured to shift between a collapsed configuration and an expanded configuration, and an occlusive disk element disposed within the disk portion. The disk portion may include a first disk portion integrally formed with the body portion, and a second disk portion movably attached to the first disk portion by at least one hinge member.

19 Claims, 11 Drawing Sheets

(56) References Cited

U.S. PATENT DOCUMENTS

| | | |
|---|---|---|
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Lentz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |

(56) References Cited

U.S. PATENT DOCUMENTS

| | | |
|---|---|---|
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muij Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |

(56) References Cited

U.S. PATENT DOCUMENTS

| | | |
|---|---|---|
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | Van Tassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,100,938 B2 | 1/2012 | Figulla et al. |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,728,117 B1 | 5/2014 | Janardhan et al. |
| 8,758,389 B2 | 6/2014 | Glimsdale |
| 8,828,051 B2 | 9/2014 | Javois et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,211,124 B2 | 12/2015 | Campbell et al. |
| 9,295,472 B2 | 3/2016 | Ottma |
| 9,351,716 B2 | 5/2016 | Miles et al. |
| 9,445,895 B2 | 9/2016 | Kreidler |
| 9,554,804 B2 | 1/2017 | Erzberger et al. |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,592,058 B2 | 3/2017 | Erzberger et al. |
| 9,597,088 B2 | 3/2017 | Ottma |
| 9,629,636 B2 | 4/2017 | Fogarty et al. |
| 9,730,701 B2 | 8/2017 | Tischler et al. |
| 9,743,932 B2 | 8/2017 | Amplatz et al. |
| 9,750,505 B2 | 9/2017 | Miles et al. |
| 9,763,666 B2 | 9/2017 | Wu et al. |
| 9,795,387 B2 | 10/2017 | Miles et al. |
| 9,808,253 B2 | 11/2017 | Li et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 10,201,337 B2 | 2/2019 | Glimsdale |
| 10,231,737 B2 | 3/2019 | Amplatz et al. |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0212432 A1 | 11/2003 | Khairkhahan et al. |
| 2003/0220667 A1 | 11/2003 | van der Burg et al. |
| 2004/0034366 A1 | 2/2004 | van der Burg et al. |
| 2004/0044361 A1* | 3/2004 | Frazier ............... A61B 17/0057 606/200 |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |

(56) References Cited

U.S. PATENT DOCUMENTS

| | | |
|---|---|---|
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2006/0247680 A1 | 11/2006 | Amplatz et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0112380 A1 | 5/2007 | Figulla et al. |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0276086 A1* | 11/2011 | Al-Qbandi ......... A61B 17/0057 606/213 |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0271337 A1 | 10/2012 | Figulla et al. |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0131717 A1 | 5/2013 | Glimsdale |
| 2013/0165735 A1 | 6/2013 | Khairkhahan et al. |
| 2013/0211492 A1 | 8/2013 | Schneider et al. |
| 2013/0296912 A1 | 11/2013 | Ottma |
| 2013/0331884 A1 | 12/2013 | Van der Burg et al. |
| 2014/0005714 A1 | 1/2014 | Quick et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0214077 A1 | 7/2014 | Glimsdale |
| 2014/0296908 A1 | 10/2014 | Ottma et al. |
| 2014/0303719 A1 | 10/2014 | Cox et al. |
| 2014/0309684 A1* | 10/2014 | Al-Qbandi ......... A61B 17/0057 606/213 |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0015397 A1 | 1/2016 | Figulla et al. |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0007262 A1 | 1/2017 | Amplatz et al. |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0119400 A1 | 5/2017 | Amplatz et al. |
| 2017/0181751 A1 | 6/2017 | Larsen et al. |
| 2017/0340336 A1 | 11/2017 | Osypka |
| 2017/0354421 A1 | 12/2017 | Maguire et al. |
| 2018/0064446 A1 | 3/2018 | Figulla et al. |
| 2018/0070950 A1 | 3/2018 | Zaver et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2019/0133563 A1 | 5/2019 | Glimsdale |
| 2019/0175185 A1 | 6/2019 | Amplatz et al. |
| 2019/0223883 A1 | 7/2019 | Anderson et al. |
| 2019/0247053 A1 | 8/2019 | Inouye |

FOREIGN PATENT DOCUMENTS

| | | |
|---|---|---|
| CN | 104287804 A | 1/2015 |
| CN | 104352261 A | 2/2015 |
| CN | 106859722 A | 6/2017 |
| CN | 109464173 A | 3/2019 |
| DE | 102010004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| EP | 3398523 A1 | 11/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |

(56) References Cited

FOREIGN PATENT DOCUMENTS

| | | |
|---|---|---|
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al, "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation to Pay Additional Fees and, Where Applicable, Protest Fee, dated Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 2020 for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation to Pay Additional Fees dated Feb. 22, 2019 for International Application No. PCT/US2018/066163.
International Search Report and Written Opinion dated Oct. 23, 2020 for International Application No. PCT/US2020/042192.
International Search Report and Written Opinion dated Oct. 13, 2020 for International Application No. PCT/US2020/048437.

\* cited by examiner

LEFT ATRIAL APPENDAGE IMPLANT WITH SEALING DISK

CROSS-REFERENCE TO RELATED APPLICATIONS

This application claims the benefit of priority of U.S. Provisional Application No. 62/894,296 filed Aug. 30, 2019, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices and introducers as well as alternative methods for manufacturing and using medical devices and introducers.

SUMMARY

In a first aspect, an implant for occluding a left atrial appendage may comprising an expandable framework including a body portion and a disk portion, wherein the expandable framework may be configured to shift between a collapsed configuration and an expanded configuration, and an occlusive disk element disposed within the disk portion. The disk portion may include a first disk portion integrally formed with the body portion, and a second disk portion movably attached to the first disk portion by at least one hinge member.

In addition or alternatively to any aspect herein, the second disk portion is structurally independent of the first disk portion.

In addition or alternatively to any aspect herein, the second disk portion includes a proximal hub configured to releasably connect the implant to a delivery device.

In addition or alternatively, the first disk portion is oriented substantially transverse to a central longitudinal axis of the body portion in the expanded configuration.

In addition or alternatively to any aspect herein, at least half of the first disk portion is substantially planar in the expanded configuration.

In addition or alternatively to any aspect herein, the second disk portion is oriented substantially transverse to a central longitudinal axis of the body portion in the expanded configuration.

In addition or alternatively to any aspect herein, at least half of the second disk portion is substantially planar in the expanded configuration.

In addition or alternatively to any aspect herein, the occlusive disk element is sandwiched between the first disk portion and the second disk portion in the expanded configuration.

In addition or alternatively to any aspect herein, the disk portion has an oblong perimeter shape in the expanded configuration.

In addition or alternatively, an implant for occluding a left atrial appendage may comprise an expandable framework including a body portion and a disk portion, wherein the expandable framework may be configured to shift between a collapsed configuration and an expanded configuration, and an occlusive disk element coupled to the disk portion by at least one hinge member.

In addition or alternatively to any aspect herein, the disk portion may include a first disk portion integrally formed with the body portion, and a second disk portion movably attached to the first disk portion by the at least one hinge member.

In addition or alternatively to any aspect herein, the occlusive disk element is disposed between the first disk portion and the second disk portion.

In addition or alternatively to any aspect herein, each of the at least one hinge member includes a coiled element.

In addition or alternatively to any aspect herein, the coiled element includes a piercing point on at least one end.

In addition or alternatively to any aspect herein, the disk portion is disposed proximal of the body portion.

In addition or alternatively, an implant for occluding a left atrial appendage may comprise an expandable framework including a body portion and a disk portion, wherein the expandable framework may be configured to shift between a collapsed configuration and an expanded configuration, and an occlusive disk element disposed within the disk portion. The disk portion may include a first disk portion integrally formed with the body portion, and a second disk portion pivotably attached to the first disk portion by at least one hinge member encircling at least a portion of the first disk portion and at least a portion of the second disk portion. The occlusive disk element may be coupled to the disk portion by the at least one hinge member.

In addition or alternatively to any aspect herein, the first disk portion includes a first pocket disposed along a perimeter of the first disk portion, and the second disk portion includes a second pocket disposed along a perimeter of the second disk portion, wherein the first pocket is aligned with the second pocket in the expanded configuration to form a pocket assembly.

In addition or alternatively to any aspect herein, the at least one hinge member is positioned within the first pocket and the second pocket.

In addition or alternatively to any aspect herein, the first disk portion includes a plurality of first pockets disposed along the perimeter of the first disk portion, and the second disk portion includes a plurality of second pockets disposed along the perimeter of the second disk portion. The plurality of first pockets may be aligned with the plurality of second pockets to form a plurality of pocket assemblies, wherein one hinge member is positioned within each pocket assembly.

In addition or alternatively to any aspect herein, the disk portion is spaced apart from the body portion by a neck portion.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
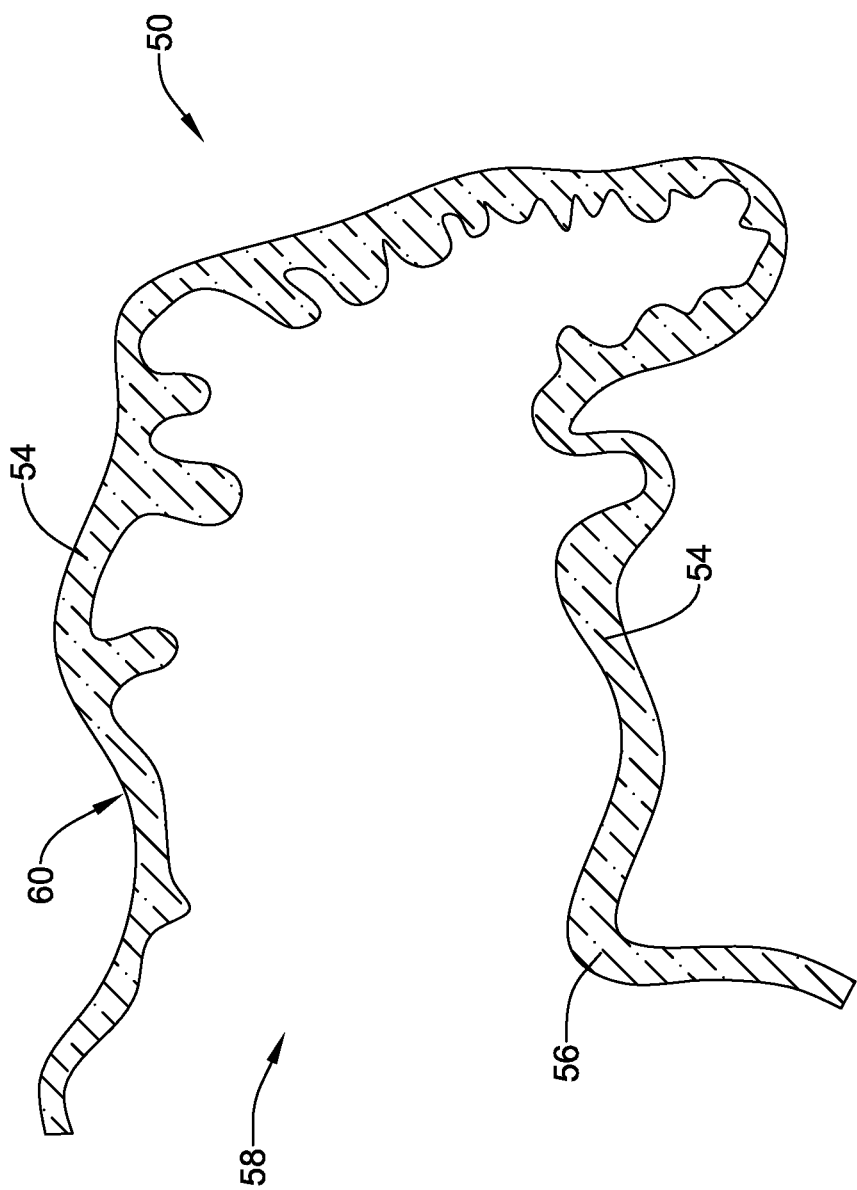
FIG. 1 is a schematic partial cross-sectional view of an example left atrial appendage.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 is a partial cross-sectional view of an example left atrial appendage 50, which may be attached to and in fluid communication with a left atrium of a patient's heart. In some patients, the left atrial appendage 50 may have a complex geometry and/or irregular surface area. Those skilled in the art will recognize that the illustrated left atrial appendage is merely one of many possible shapes and sizes for the left atrial appendage, which may vary from patient to patient. Those of skill in the art will also recognize that the medical devices and methods disclosed herein may be adapted for various sizes and shapes of the left atrial appendage, as necessary. The left atrial appendage 50 may include a generally longitudinal axis arranged along a depth of a main body 60 of the left atrial appendage 50. The main body 60 may include a wall 54 and an ostium 56 forming a proximal mouth 58. In some embodiments, a lateral extent of the ostium 56 and/or the wall 54 may be smaller or less than a depth of the main body 60 along the longitudinal axis, or a depth of the main body 60 may be greater than a lateral extent of the ostium 56 and/or the wall 54. In some embodiments, the left atrial appendage 50 may include a tail-like element associated with a distal portion of the main body 60, which element may protrude radially or laterally away from the main body 60.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

Figure 2:
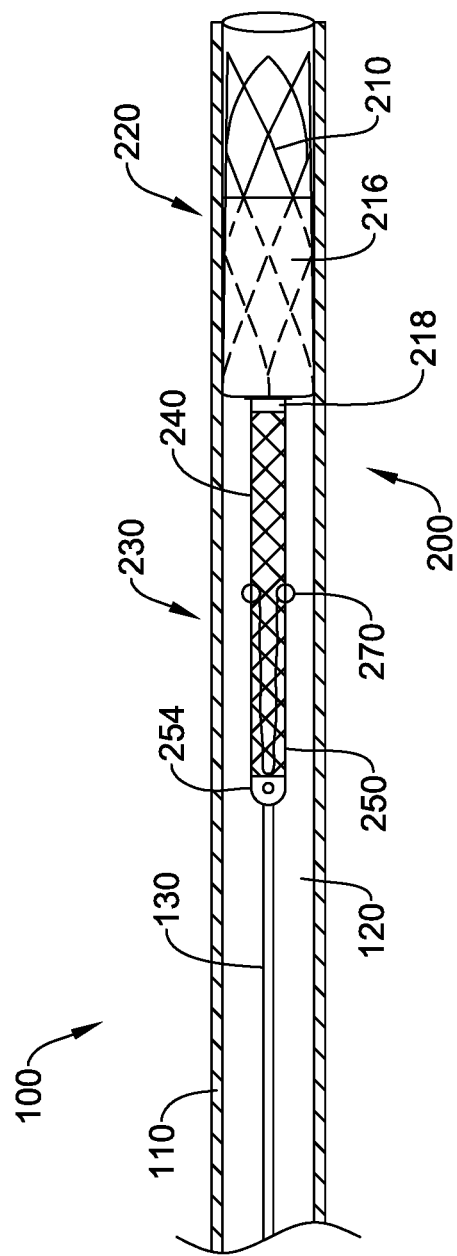
FIG. 2 illustrates aspects of a delivery device and an implant for occluding a left atrial appendage.

FIG. 2 is a partial cross-sectional view illustrating elements of a delivery device 100 and an implant 200 for occluding the left atrial appendage 50. The delivery device 100 may include a delivery sheath 110 having a lumen 120 extending to a distal end of the delivery sheath 110 and a core wire 130 slidably disposed within the lumen 120. The core wire 130 may be configured to and/or may be capable of axially translating the implant 200 relative to the delivery sheath 110. The delivery sheath 110 and/or the core wire 130 may have a selected level of axial stiffness and/or pushability characteristics while also having a selected level of flexibility to permit navigation through the patient's vasculature. Some suitable, but non-limiting, examples of materials for the delivery sheath 110 and the core wire 130 are discussed below.

The implant 200 may comprise an expandable framework 210 configured to shift between a collapsed configuration and an expanded configuration. The expandable framework 210 may be configured to releasably connect the implant 200 to the delivery device 100. The expandable framework 210 may include a body portion 220 and a disk portion 230. In some embodiments, the disk portion 230 may be spaced apart from the body portion 220 by a neck portion 214 (e.g., FIGS. 8-9). In at least some embodiments, the disk portion 230 may be secured to, attached to, and/or connected to the body portion 220 by the neck portion 214. In some embodiments, the neck portion 214 is tubular (e.g., a tubular member, annular, etc.) and includes a lumen extending therethrough. In some embodiments, the neck portion 214 may be integrally formed with the body portion 220 as a unitary structure. For example, the neck portion 214 may be formed from the same structural elements (e.g., cut tube, braided filaments, etc.) as the body portion 220. The disk portion 230 may be disposed proximal of the body portion 220. Additional details related to the disk portion 230 are described below.

When the implant 200 is disposed within the lumen 120 of the delivery sheath 110, the expandable framework 210 may be held and/or disposed in the collapsed configuration, as shown in FIG. 2 for example. The body portion 220 and the disk portion 230 may be configured to shift between the collapsed configuration (e.g., FIG. 2) and the expanded configuration (e.g., FIG. 3). In some embodiments, the implant 200 may optionally include an occlusive body element 216 disposed and/or positioned on, over, and/or around at least a portion of the expandable framework 210. For example, the implant 200 may optionally include an occlusive body element 216 (e.g., a mesh, a fabric, a membrane, and/or other surface treatment) disposed and/or positioned on, over, and/or around at least a portion of the body portion 220 of the expandable framework 210. In at least some embodiments, the occlusive body element 216 may be secured to, attached to, and/or connected to the expandable framework 210 and/or the body portion 220 of the expandable framework 210. In some embodiments, the occlusive body element 216 may be secured to, attached to, and/or connected to the expandable framework 210 and/or the body portion 220 of the expandable framework 210 at a plurality of discrete locations.

In some embodiments, the occlusive body element 216 may be porous. In some embodiments, the occlusive body element 216 may be non-porous. In some embodiments, the occlusive body element 216 may be designed, sized, and/or configured to prevent thrombus and/or embolic material from passing out of the left atrial appendage 50 into the left atrium and/or the patient's bloodstream. In some embodiments, the occlusive body element 216 may be configured to promote endothelization. In at least some embodiments, the occlusive body element 216 may be secured to the neck portion 214 by an annular marker band 218 (e.g., FIGS. 2, 8-9). In some embodiments, the occlusive body element 216 may be adhesively bonded to the annular marker band 218. In some embodiments, the annular marker band 218 may be embedded within the occlusive body element 216. The annular marker band 218 may be formed from and/or doped with a radiopaque material for improved visualization. In some embodiments, the annular marker band 218 may compress, pinch, and/or otherwise gather the neck portion 214 tightly together to reduce and/or minimize fluid passage and/or leakage through the neck portion 214. Some suitable, but non-limiting, examples of materials for the occlusive body element 216 and the annular marker band 218 are discussed below.

The disk portion 230 may include a first disk portion 240 and a second disk portion 250 movably attached to the first disk portion 240 by at least one hinge member 270. The disk portion 230 may extend proximally from the body portion 220 in the collapsed configuration and/or within the lumen 120 of the delivery sheath 110 to a proximal hub 254. In some embodiments, the second disk portion 250 may include the proximal hub 254. The proximal hub 254 may be configured to releasably connect and/or attach the implant 200 to the core wire 130 of the delivery device 100. In some embodiments, the proximal hub 254 may include internal threads configured to rotatably and/or threadably engage an externally threaded distal end 132 of the core wire 130 (e.g., FIG. 9). Other configurations for releasably connecting the implant 200 to the core wire 130 are also contemplated.

Figure 3:
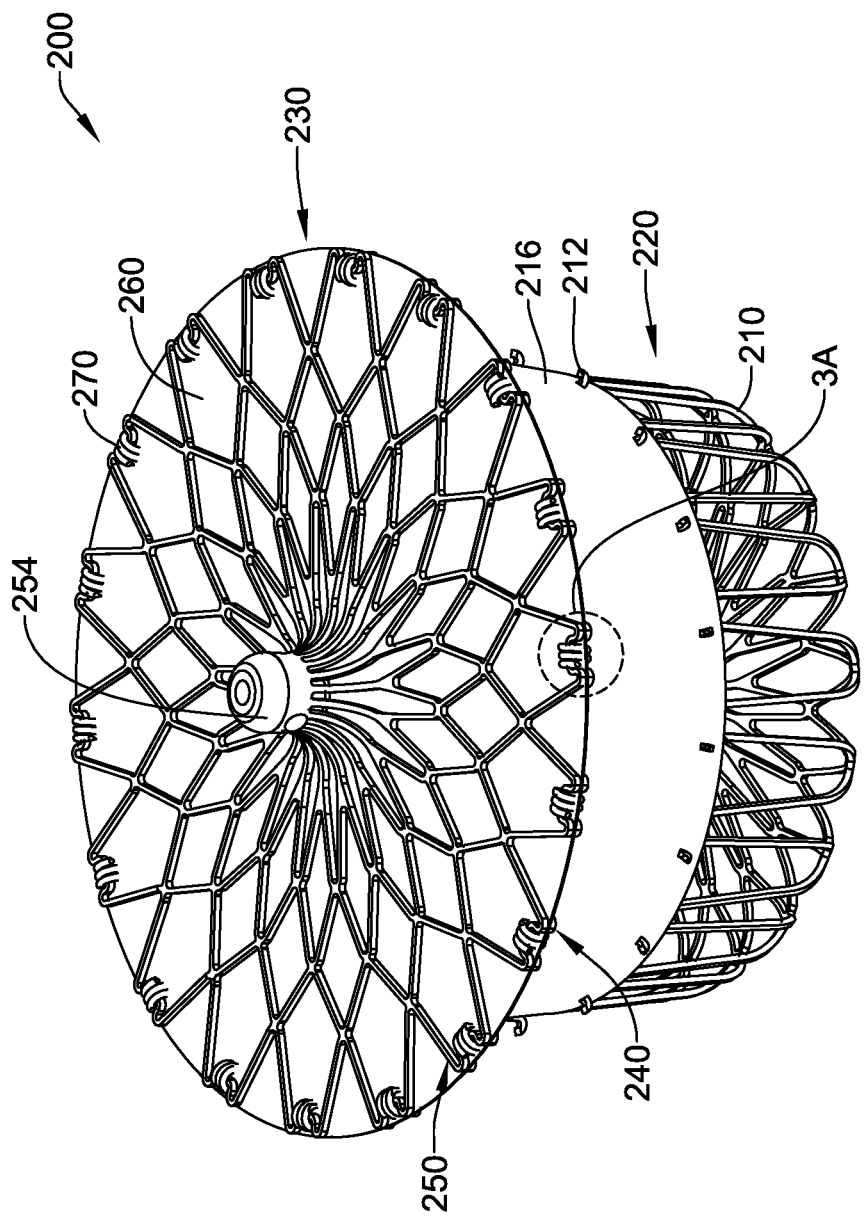
FIGS. 3 and 3A illustrate aspects of the implant for occluding a left atrial appendage.

In at least some embodiments, the expandable framework 210 and/or the body portion 220 of the expandable framework 210 may include a plurality of anchor members 212 extending outward from the expandable framework 210 and/or the body portion 220, as seen in FIG. 3. The plurality of anchor members 212 may be configured to engage with the wall 54 of the main body 60 of the left atrial appendage 50 (e.g., FIGS. 8-9). In some embodiments, the plurality of anchor members 212 may be formed as J-shaped hooks having a free end extending in and/or directed toward a proximal direction with respect to a central longitudinal axis of the expandable framework 210. Other configurations are also contemplated. In some embodiments, the plurality of anchor members 212 may extend through the occlusive body element 216, where present, as shown in FIG. 3. Some suitable, but non-limiting, examples of materials for the expandable framework 210, the plurality of anchor members 212, the body portion, the disk portion 230, etc. are discussed below.

Figure 4:
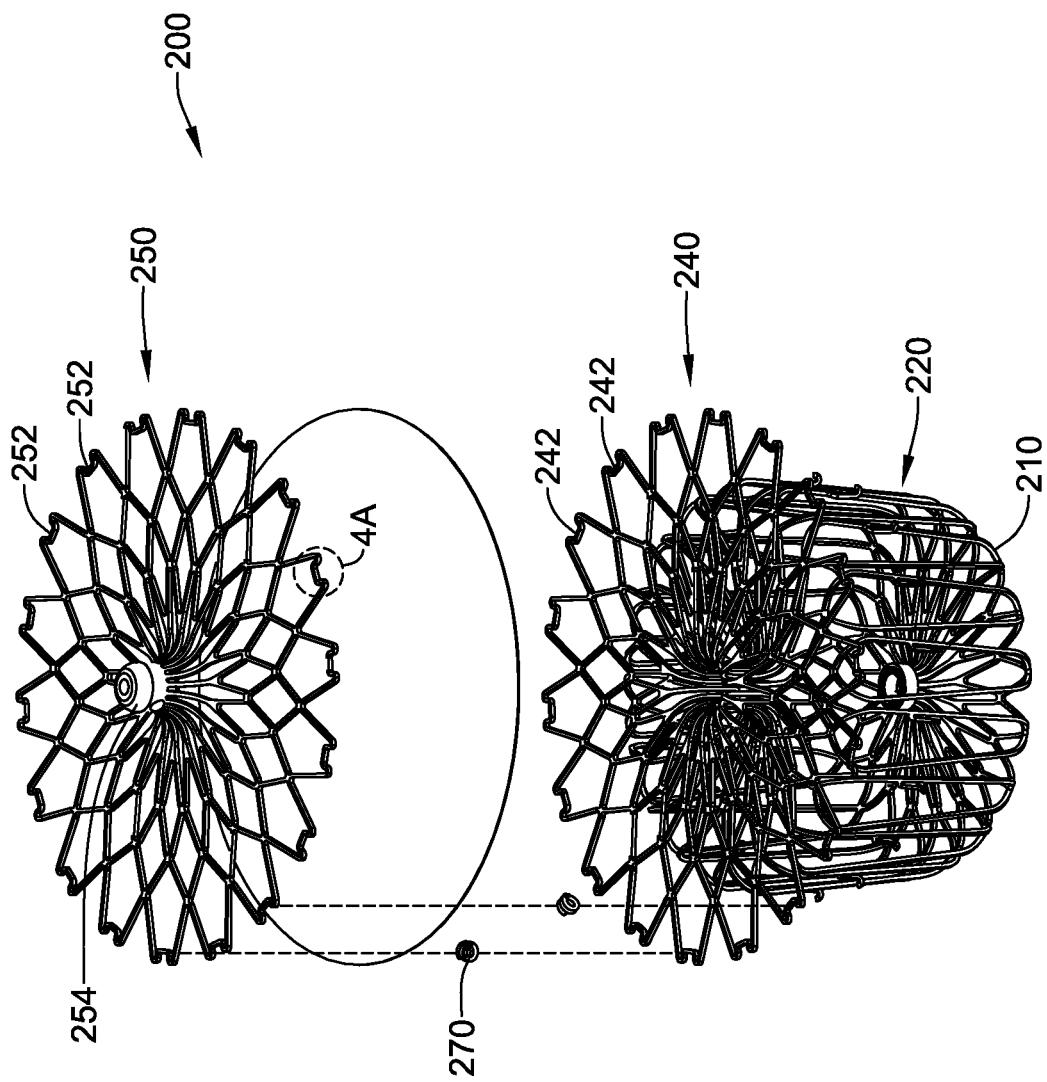
FIG. 4 is a partial exploded view of the implant of FIG. 3.

As shown in FIGS. 3-4, the disk portion 230 may include the first disk portion 240 and the second disk portion 250. In at least some embodiments, the first disk portion 240 may be integrally formed with the neck portion 214 and/or the body portion 220 (e.g., FIGS. 8-9). For example, in some embodiments, the body portion 220 may include the neck portion 214, or the first disk portion 240 may include the neck portion 214. Additionally, in at least some embodiments, the body portion 220, the neck portion 214, and the first disk portion 240 may be integrally formed as a single unitary structure. In some embodiments, the second disk portion 250 may be structurally independent of the first disk portion 240. For example, the first disk portion 240 and the second disk portion 250 may be formed as separate pieces or structures, and/or the first disk portion 240 and the second disk portion 250 may be formed independently of each other. In some embodiments, the second disk portion 250 may be disposed proximally of the first disk portion 240. The first disk portion 240 and the second disk portion 250 may be disposed proximally of the body portion 220 in the collapsed configuration and/or in the expanded configuration. In some embodiments, the proximal hub 254 may be disposed coaxially with and/or may be axially aligned with the central longitudinal axis of the expandable framework 210.

In some embodiments, the implant 200 may include an occlusive disk element 260 (e.g., a mesh, a fabric, a membrane, and/or other surface treatment) configured to promote endothelization on and/or across the disk portion 230. In some embodiments, the implant 200 may include the occlusive disk element 260 disposed on and/or surrounding a portion of an outer surface of the disk portion 230. In some embodiments, the implant 200 may include the occlusive disk element 260 disposed within the disk portion 230. In some embodiments, the occlusive disk element 260 may be disposed and/or sandwiched between the first disk portion 240 and the second disk portion 250 in the expanded configuration. In some embodiments, the occlusive disk element 260 may be elastic and/or stretchable to accommodate changes in shape and/or size of the disk portion 230 when the disk portion 230 are shifted toward and/or into the expanded configuration.

In some embodiments, the occlusive disk element 260 may be porous. In some embodiments, the occlusive disk element 260 may be non-porous. In some embodiments, the occlusive disk element 260 may be designed, sized, and/or configured to prevent thrombus and/or embolic material from passing out of the left atrial appendage 50 into the left atrium and/or the patient's bloodstream. In some embodiments, the occlusive disk element 260 may be configured to promote endothelization across the ostium 56 and/or the proximal mouth 58 of the left atrial appendage 50 to effectively remove the left atrial appendage 50 from the patient's bloodstream. Some suitable, but non-limiting, examples of materials for the occlusive disk element 260 are discussed below.

Figure 3A:
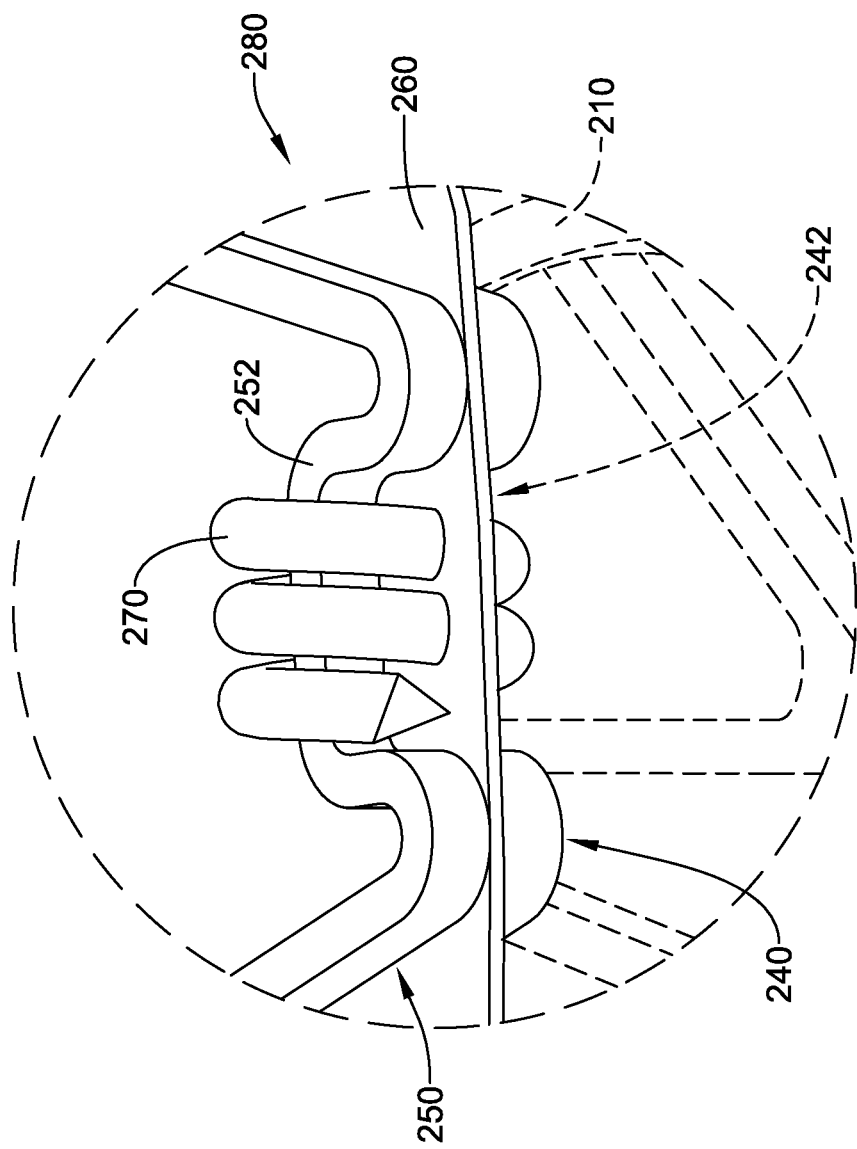

In some embodiments, the second disk portion 250 may be movably and/or pivotably attached to the first disk portion 240 by at least one hinge member 270, as shown in greater detail in FIG. 3A. In some embodiments, the at least one hinge member 270 may encircle at least a portion of the first disk portion 240 and at least a portion of the second disk portion 250. In some embodiments, the first disk portion 240 may include a first pocket 242 disposed along a perimeter of the first disk portion 240. In some embodiments, the second disk portion 250 may include a second pocket 252 disposed along a perimeter of the second disk portion 250. In some embodiments, the first pocket 242 may be aligned with the second pocket 252 in the expanded configuration to form a pocket assembly 280. In some embodiments, the at least one hinge member 270 may be positioned within the first pocket 242 and the second pocket 252.

In some embodiments, the first disk portion 240 may include a plurality of first pockets 242 disposed along the perimeter of the first disk portion 240, as seen in the partially exploded view of FIG. 4. In some embodiments, the second disk portion 250 may include a plurality of second pockets 252 disposed along the perimeter of the second disk portion 250. In some embodiments, the plurality of first pockets 242 may be aligned with the plurality of second pockets 252 in the expanded configuration to form a plurality of pocket assemblies 280, wherein one hinge member 270 is positioned within each pocket assembly 280, as shown in FIGS. 3 and 3A.

In at least some embodiments, the occlusive disk element 260 may be coupled to the disk portion 230 by the at least one hinge member 270. In some embodiments, the occlusive disk element 260 may be coupled to the first disk portion 240 and/or the second disk portion 250 by the at least one hinge member 270. In some embodiments, the occlusive disk element 260 may be coupled to the disk portion 230 by other and/or additional means, including but not limited to, sutures or filaments, adhesive bonding, encapsulation, etc. In some embodiments, the implant 200 may be devoid of any other structure or means coupling the occlusive disk element 260 to the disk portion 230 besides the at least one hinge member 270. For example, in some embodiments, only the at least one hinge member 270 may couple the occlusive disk element 260 to the disk portion 230.

In some embodiments, the first disk portion 240 may be oriented substantially transverse to the central longitudinal axis of the expandable framework 210 and/or the body portion 220 in the expanded configuration (when otherwise unconstrained and/or unstressed). In some embodiments, the first disk portion 240 may be oriented substantially perpendicular to the central longitudinal axis of the expandable framework 210 and/or the body portion 220 in the expanded configuration (when otherwise unconstrained and/or unstressed). In some embodiments, at least half (e.g. a majority) of the first disk portion 240 may be substantially planar in the expanded configuration (when otherwise unconstrained and/or unstressed). In some embodiments, the first disk portion 240 may be generally tubular or annular in the collapsed configuration. In some embodiments, the second disk portion 250 may be oriented substantially transverse to the central longitudinal axis of the expandable framework 210 and/or the body portion 220 in the expanded configuration (when otherwise unconstrained and/or unstressed). In some embodiments, the second disk portion 250 may be oriented substantially perpendicular to the central longitudinal axis of the expandable framework 210 and/or the body portion 220 in the expanded configuration (when otherwise unconstrained and/or unstressed). In some embodiments, at least half (e.g. a majority) of the second disk portion 250 may be substantially planar in the expanded configuration (when otherwise unconstrained and/or unstressed). In some embodiments, the second disk portion 250 may be generally tubular or annular in the collapsed configuration (as seen in FIG. 2 for example).

Figure 4A:
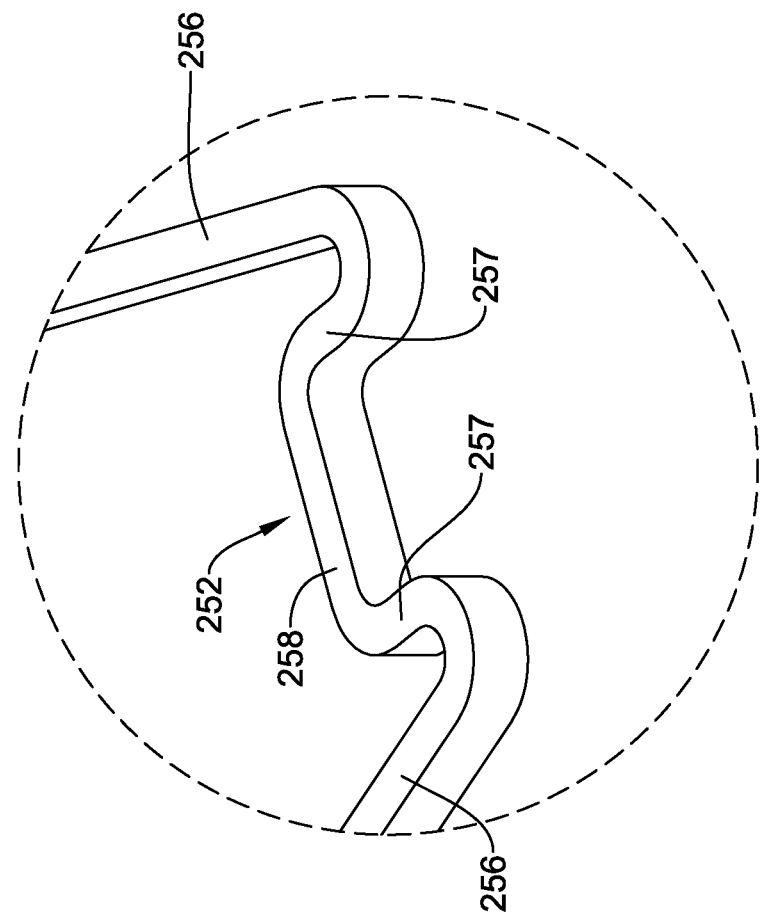
FIG. 4A illustrates aspects of an example disk portion.

Detailed FIG. 4A illustrates selected aspects of the second pocket 252 of the second disk portion 250. It will be readily understood that the same features and/or aspects also apply to the first pocket 242 of the first disk portion 240. The second disk portion 250 may include and/or may be formed from a plurality of interconnected struts 256 extending away from the central longitudinal axis of the implant 200 and/or the expandable framework 210 toward the perimeter of the second disk portion 250 in the expanded configuration. Each instance of the second pocket 252 may be formed from two adjacent interconnected struts 256. At the perimeter of the second disk portion 250, each of the adjacent interconnected struts 256 may bend back toward the central longitudinal axis of the implant 200 and/or the expandable framework 210 in the expanded configuration to form a radially extending segment 257. The adjacent radially extending segments 257 maybe joined and/or connected by a circumferentially extending segment 258 to form a continuous portion of the expandable framework 210 and/or the second disk portion 250. In some embodiments, a length of the radially extending segment 257 may be at least about 75%, at least about 100%, at least about 125%, at least about 150%, at least about 200%, etc. of a thickness 274 of the at least one hinge member 270 (e.g., FIG. 5). In some embodiments, the length of the radially extending segment 257 may be greater than an inner extent and/or an inner diameter of the at least one hinge member 270. In some embodiments, a length of the circumferentially extending segment 258 may be from about 80% to about 120% of a length of the at least one hinge member 270. As such, the at least one hinge member 270 may be captured within the second pocket 252 between the two adjacent radially extending segments 257 when the hinge member 270 is disposed on and/or around the circumferentially extending segment 258.

Figure 5:
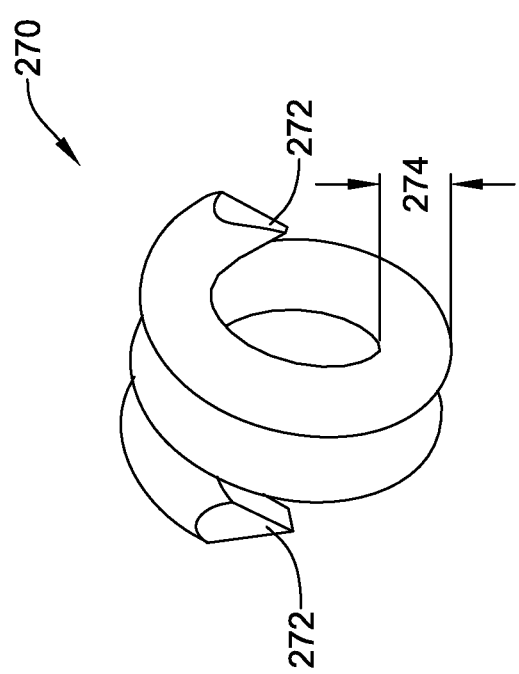
FIG. 5 illustrates aspects of an example hinge member.

FIG. 5 illustrates an example configuration of the at least one hinge member 270. Any and/or all related description herein may apply to one, more than one, each, and/or all instances of the at least one hinge member 270. In some embodiments, the at least one hinge member 270 may include a coiled element. In some embodiments, each of the at least one hinge member 270 may include a coiled element. In some embodiments, the coiled element may include a piercing point 272 on at least one end. In some embodiments, the coiled element may include the piercing point 272 on both ends, opposing ends, each end, etc. of the coiled element. The piercing point 272 may be configured to and/or be capable of piercing the occlusive disk element 260 during assembly of the implant 200 to couple the occlusive disk element 260 to the disk portion 230. The at least one hinge member 270 and/or the coiled element may have a thickness 274 defined by a cross-sectional dimension of an individual winding of the at least one hinge member 270 and/or the coiled element. While the at least one hinge member 270 and/or the coiled element is illustrated as a wire having a round outer profile, other configurations, include rectangular, polygonal, or irregular outer profiles, are also contemplated. Some suitable, but non-limiting, examples of materials for the at least one hinge member 270 are discussed below.

Figure 6:
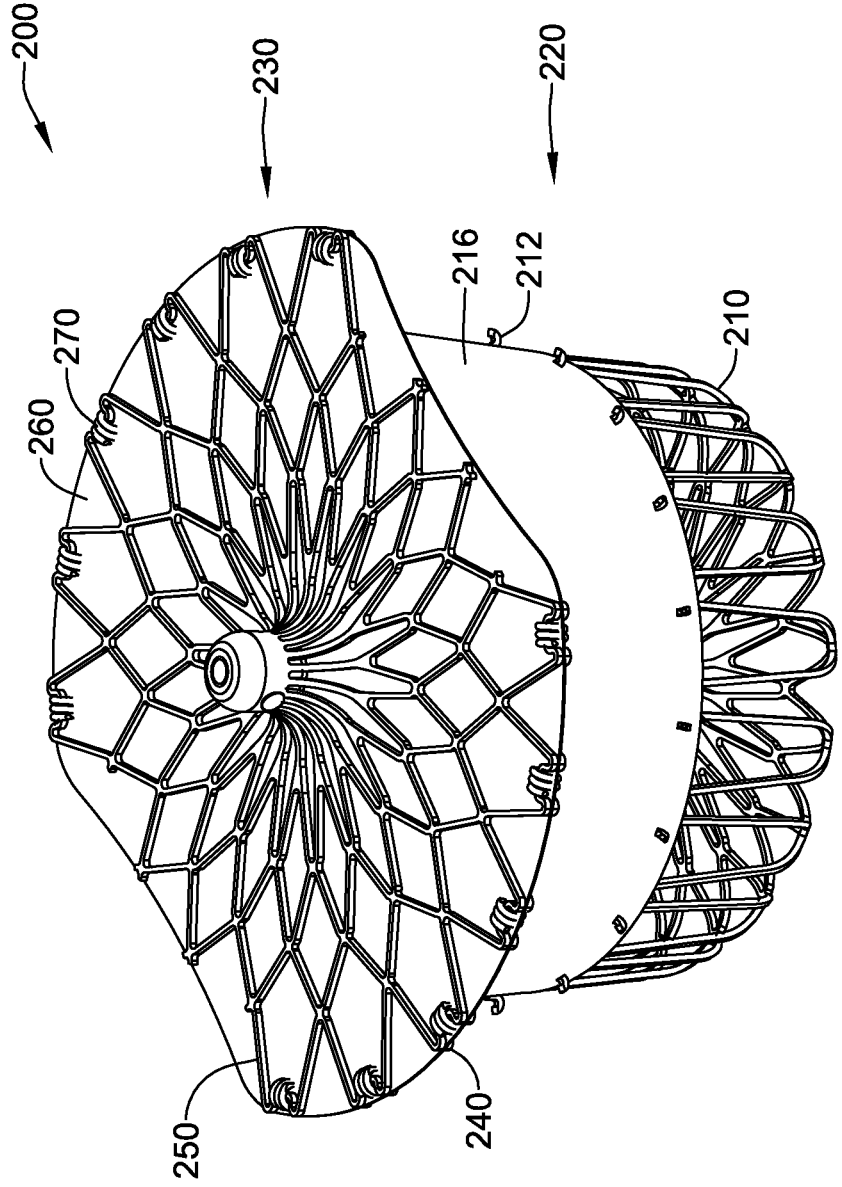
FIG. 6 illustrates aspects of an alternative configuration of the implant for occluding a left atrial appendage.
Figure 7:
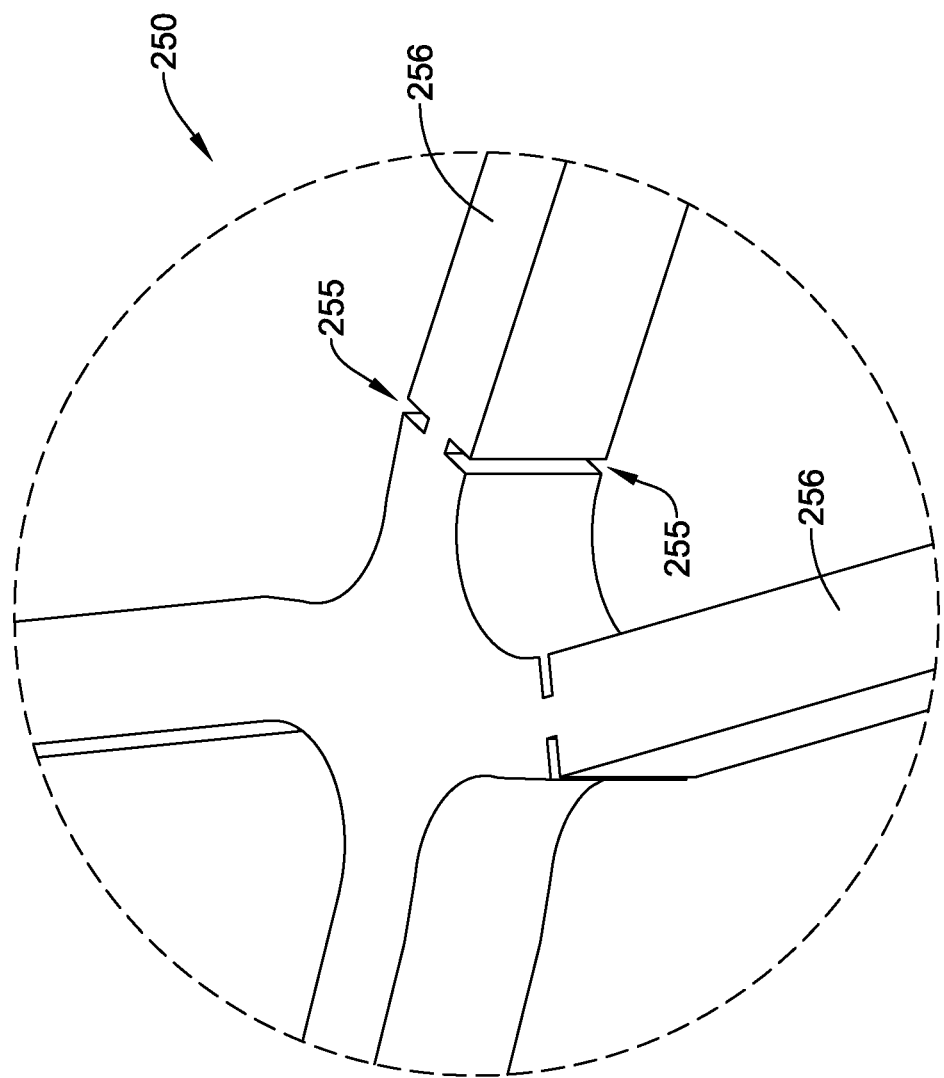
FIG. 7 illustrates aspects of the alternative configuration of the implant illustrated in FIG. 6.

FIG. 6 illustrates an alternative configuration of the disk portion 230. In some embodiments, the disk portion 230, including the first disk portion 240 and the second disk portion 250, may have an oblong perimeter shape in the expanded configuration. The oblong perimeter shape may permit the implant 200 to better fit asymmetrical and/or irregular anatomies. In some embodiments, the disk portion 230 may be made by forming and/or adding notches 255 in the struts 256 of the first pocket(s) 242 and the second pocket(s) 252 corresponding to and/or intended to be aligned with the first pocket(s) 242 during manufacture of the first disk portion 240 and the second disk portion 250, respectively, and/or during assembly of the disk portion 230, as shown in FIG. 7. The notches 255 may weaken the struts 256 to permit removal of the desired first pocket(s) 242 and the second pocket(s) 252 corresponding to and/or intended to be aligned with the first pocket(s) 242, such as by hand and/or without further mechanical assistance, for example. In embodiments having the alternative configuration of the disk portion 230 described herein, the occlusive disk element 260 may also be trimmed to an oblong shape matching and/or corresponding to the oblong perimeter shape of the disk portion 230.

Figure 8:
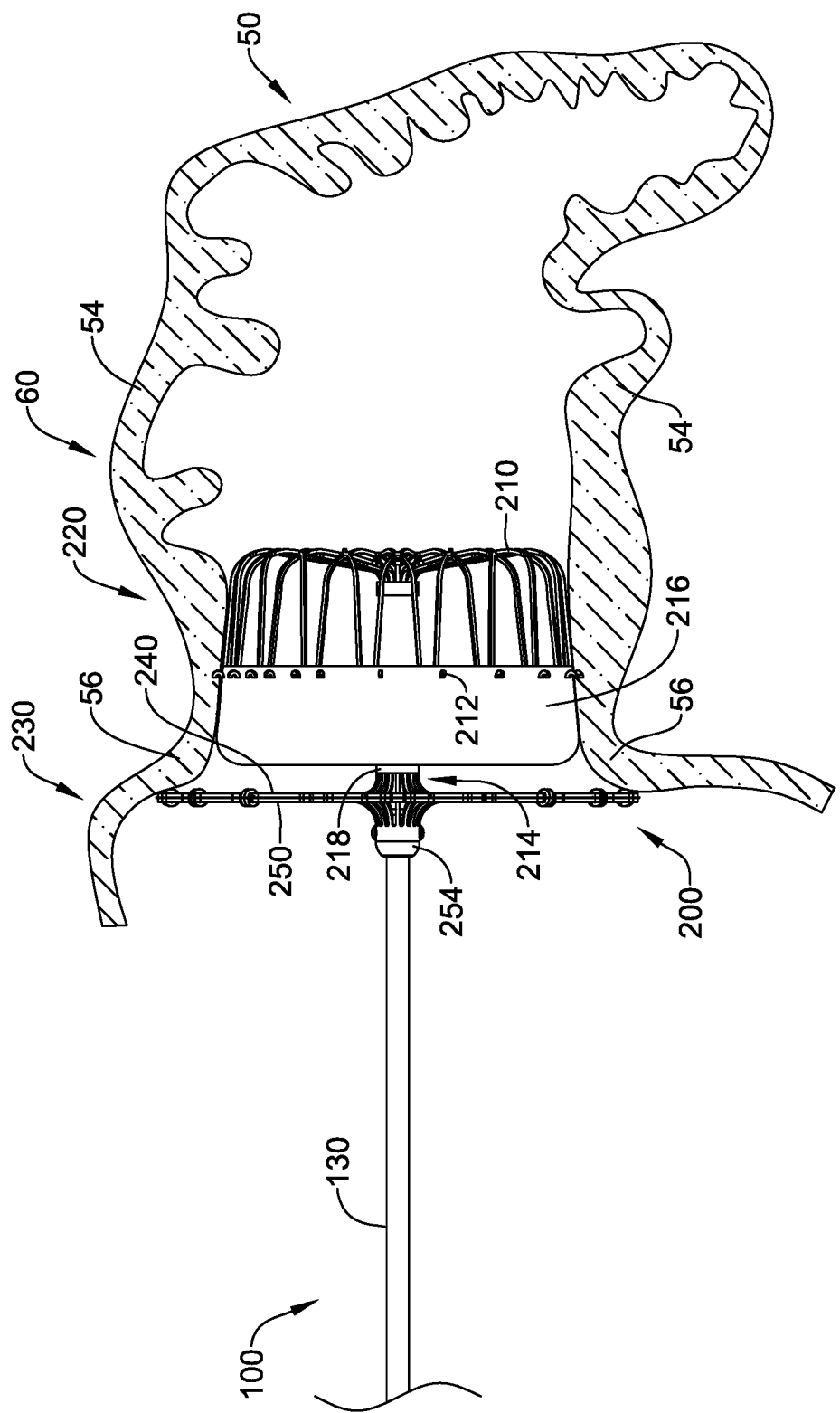
FIGS. 8-9 illustrate placement of an example implant of the disclosure within the left atrial appendage.

A method for occluding the left atrial appendage 50 may comprise advancing the implant 200 into the left atrial appendage 50. For example, the implant 200 may be advanced to the left atrial appendage 50 within the lumen 120 of the delivery sheath 110 in the collapsed configuration. The method includes deploying the expandable framework 210 from the delivery sheath 110 within the left atrial appendage 50. The method further includes expanding and/or shifting the expandable framework 210 from the collapsed configuration to the expanded configuration within the left atrial appendage 50. In the expanded configuration, the expandable framework 210 may be urged into contact with, engaged with, and/or anchored to the wall 54 of the main body 60 of the left atrial appendage 50, as seen in FIG. 8. Additionally, the method may include deploying and/or expanding the disk portion 230 from the collapsed configuration to the expanded configuration proximate the ostium 56 of the left atrial appendage 50. In some embodiments, the method may include deploying and/or expanding the disk portion 230 to engage the wall 54 and/or the ostium 56 of the left atrial appendage 50 in a sealing manner. In at least some embodiments, the disk portion 230 may span across the ostium 56 of the left atrial appendage 50. In some embodiments, the disk portion 230 may span completely across the ostium 56 of the left atrial appendage 50, thereby effectively removing the left atrial appendage 50 from the circulatory system of the patient.

In some embodiments, the disk portion 230 may be spaced apart proximally from the expandable framework 210 by a gap distance. The gap distance may be generally understood as the axial distance between a proximal surface of the expandable framework 210 and a distal surface of the disk portion 230 measured generally parallel to a central longitudinal axis of the implant 200, the expandable framework 210, and/or the disk portion 230. In some embodiments, the gap distance may be fixed. In some embodiments, the gap distance may be variable. In some embodiments, the gap distance may be defined by the neck portion 214.

The expandable framework 210 and/or the plurality of anchor members 212 may function as an anchoring mechanism for the disk portion 230. In some embodiments, the delivery device 100 and/or the implant 200 may include at least one means of adjusting the gap distance. In some embodiments, the method for occluding the left atrial appendage 50 may comprise adjusting the gap distance to position the disk portion 230 against and/or within the ostium 56 of the left atrial appendage 50. In some embodiments, the at least one means of adjusting the gap distance may be configured to translate the disk portion 230 towards and/or into the ostium 56 of the left atrial appendage 50. For example, upon initial deployment of the implant 200, the disk portion 230 may be spaced apart from the ostium 56 of the left atrial appendage 50. In some embodiments, the implant 200 and/or the expandable framework 210 may be advanced deeper into the main body 60 of the left atrial appendage 50 until the disk portion 230 engages the ostium 56 of the left atrial appendage. In some embodiments, the at least one means of adjusting the gap distance may be used to translate the disk portion 230 towards and/or into the ostium 56 of the left atrial appendage 50. In one example, the gap distance may be shortened by about 10%, about 20%, about 25%, about 30%, about 40%, about 50%, about 60%, about 75%, etc. from its initial deployment distance. In another example, the gap distance may be shortened or reduced to zero.

In some embodiments, the disk portion 230 may be oriented at an oblique angle to the central longitudinal axis of the expandable framework 210. In some embodiments, the neck portion 214 may be flexible and/or may permit off-axis orientation of the disk portion 230 relative to the expandable framework 210, which may ease positioning, implantation, and/or sealing within an irregularly shaped and/or oriented left atrial appendage 50.

Figure 9:
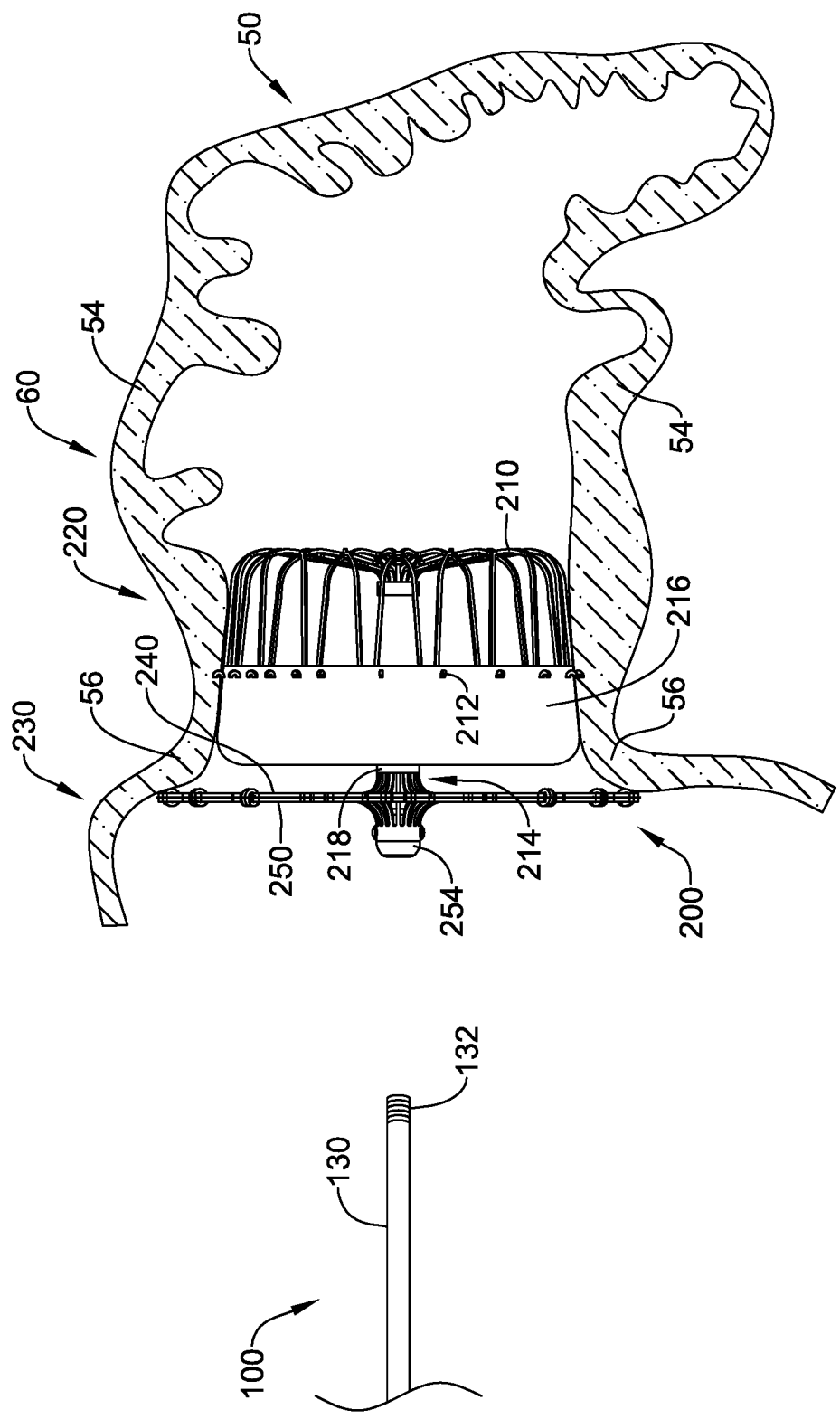

When satisfied with the positioning of the body portion 220 within the left atrial appendage 50 and/or the disk portion 230 against the ostium 56 of the left atrial appendage 50, the delivery device 100 may be disconnected from the implant 200, as seen in FIG. 9, thereby leaving the implant 200 disposed at and/or in the left atrial appendage 50. In some embodiments, disconnecting the delivery device 100 from the implant 200 may include rotating the externally threaded distal end 132 of the core wire 130 relative to the implant 200 and/or the proximal hub 254 to disengage the core wire 130 from the implant 200.

In some embodiments, the delivery system may include a keying structure configured to prevent rotation of the core wire 130 relative to the disk portion 230. In such embodiments, the keying structure is disengaged prior to rotating the core wire 130 relative to the implant 200 and/or the proximal hub 254. When the keying structure is engaged, rotation of the core wire 130 may be transmitted to the disk portion 230, the body portion 220, and/or the expandable framework 210. In some embodiments, rotation of the disk portion 230, the body portion 220, and/or the expandable framework 210 may facilitate positioning and/or orientation of the disk portion 230, the body portion 220, and/or the expandable framework 210 relative to the left atrial appendage 50, for example, with respect to an asymmetrical and/or irregular ostium 56 and/or left atrial appendage 50. In some embodiments, rotation of the disk portion 230, the body portion 220, and/or the expandable framework 210 may vary the gap distance by translating the disk portion 230 closer to or farther from the body portion 220 of the expandable framework 210. Other configurations, purposes, and/or results are also contemplated.

The materials that can be used for the various components of the delivery device 100 and/or the implant 200 and the various elements thereof disclosed herein may include those commonly associated with medical devices. For simplicity purposes, the following discussion refers to the delivery device 100 and/or the implant 200. However, this is not intended to limit the devices and methods described herein, as the discussion may be applied to other elements, members, components, or devices disclosed herein, such as, but not limited to, the delivery sheath 110, the core wire 130, the expandable framework 210, the plurality of anchor members 212, the neck portion 214, the occlusive body element 216, the annular marker band 218, the body portion 220, the disk portion 230, the first disk portion 240, the second disk portion 250, the proximal hub 254, the occlusive disk element 260, the at least one hinge member 270, and/or elements or components thereof.

In some embodiments, the delivery device 100 and/or the implant 200, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery device 100 and/or the implant 200, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 and/or the implant 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 and/or the implant 200 to achieve the same result.

In some embodiments, a degree of Magnetic Resonance Imaging (MM) compatibility is imparted into the delivery device 100 and/or the implant 200 and/or other elements disclosed herein. For example, the delivery device 100 and/or the implant 200, and/or components or portions thereof, may be made of a material that does not substantially distort the image and create substantial artifacts (i.e., gaps in the image). Certain ferromagnetic materials, for example, may not be suitable because they may create artifacts in an MRI image. The delivery device 100 and/or the implant 200, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the delivery device 100 and/or the implant 200 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the delivery device 100 and/or the implant 200 and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the delivery device 100 and/or the implant 200 and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An implant for occluding a left atrial appendage, comprising:
   an expandable framework including a body portion and a disk portion;
   wherein the expandable framework is configured to shift between a collapsed configuration and an expanded configuration; and
   an occlusive disk element disposed within the disk portion;
   wherein the disk portion includes:
      a first disk portion integrally formed with the body portion; and
      a second disk portion movably attached to the first disk portion by at least one hinge member.

2. The implant of claim 1, wherein the second disk portion is structurally independent of the first disk portion.

3. The implant of claim 1, wherein the second disk portion includes a proximal hub configured to releasably connect the implant to a delivery device.

4. The implant of claim 1, wherein the first disk portion is oriented substantially transverse to a central longitudinal axis of the body portion in the expanded configuration.

5. The implant of claim 4, wherein at least half of the first disk portion is substantially planar in the expanded configuration.

6. The implant of claim 1, wherein the second disk portion is oriented substantially transverse to a central longitudinal axis of the body portion in the expanded configuration.

7. The implant of claim 6, wherein at least half of the second disk portion is substantially planar in the expanded configuration.

8. The implant of claim 1, wherein the occlusive disk element is sandwiched between the first disk portion and the second disk portion in the expanded configuration.

9. The implant of claim 1, wherein the disk portion has an oblong perimeter shape in the expanded configuration.

10. An implant for occluding a left atrial appendage, comprising:
   an expandable framework including a body portion and a disk portion;
   wherein the expandable framework is configured to shift between a collapsed configuration and an expanded configuration; and
   an occlusive disk element coupled to the disk portion by at least one hinge member; and
   wherein the disk portion includes: a first disk portion integrally formed with the body portion; and a second disk portion movably attached to the first disk portion by the at least one hinge member.

11. The implant of claim 10, wherein each of the at least one hinge member includes a coiled element.

12. The implant of claim 11, wherein the coiled element includes a piercing point on at least one end.

13. The implant of claim 10, wherein the occlusive disk element is disposed between the first disk portion and the second disk portion.

14. The implant of claim 10, wherein the disk portion is disposed proximal of the body portion.

15. An implant for occluding a left atrial appendage, comprising:
   an expandable framework including a body portion and a disk portion;
   wherein the expandable framework is configured to shift between a collapsed configuration and an expanded configuration; and
   an occlusive disk element disposed within the disk portion;
   wherein the disk portion includes:
     a first disk portion integrally formed with the body portion; and
     a second disk portion pivotably attached to the first disk portion by at least one hinge member encircling at least a portion of the first disk portion and at least a portion of the second disk portion;
   wherein the occlusive disk element is coupled to the disk portion by the at least one hinge member.

16. The implant of claim 15, wherein the first disk portion includes a first pocket disposed along a perimeter of the first disk portion, and the second disk portion includes a second pocket disposed along a perimeter of the second disk portion;
   wherein the first pocket is aligned with the second pocket in the expanded configuration to form a pocket assembly.

17. The implant of claim 16, wherein the at least one hinge member is positioned within the first pocket and the second pocket.

18. The implant of claim 16, wherein the first disk portion includes a plurality of first pockets disposed along the perimeter of the first disk portion, and the second disk portion includes a plurality of second pockets disposed along the perimeter of the second disk portion;
   wherein the plurality of first pockets is aligned with the plurality of second pockets to form a plurality of pocket assemblies;
   wherein one hinge member is positioned within each pocket assembly.

19. The implant of claim 15, wherein the disk portion is spaced apart from the body portion by a neck portion.

* * * * *